United States Patent [19]

McKendry et al.

[11] 4,054,440

[45] Oct. 18, 1977

[54] 4(3H)-OXOBENZO-2,1,3-THIADIAZINE-2,2-DIOXIDES

[75] Inventors: Lennon H. McKendry, Midland, Mich.; Walter P. Bland, Takoma Park, Md.

[73] Assignee: The Dow Chemical Company, Midland, Mich.

[21] Appl. No.: 660,575

[22] Filed: Feb. 23, 1976

[51] Int. Cl.² .................... C07D 285/16; A01N 9/12
[52] U.S. Cl. .................................... 71/91; 544/11
[58] Field of Search .................. 260/243 R; 71/91

[56] References Cited

U.S. PATENT DOCUMENTS

| | | | |
|---|---|---|---|
| 3,708,277 | 1/1973 | Zeidler et al. | 260/243 |
| 3,822,257 | 7/1974 | Hamprecht et al. | 260/243 |

*Primary Examiner*—John M. Ford
*Attorney, Agent, or Firm*—Edward E. Schilling

[57] ABSTRACT

Disclosed are certain novel substituted 4(3H)-oxobenzo-2,1,3-thiadiazine-2,2-dioxide compounds and derivatives thereof and compositions and methods employing the same in the control of undesired vegetation.

33 Claims, No Drawings

4(3H)-OXOBENZO-2,1,3-THIADIAZINE-2,2-DIOXIDES

CROSS-REFERENCE TO RELATED APPLICATION

The present application describes and claims compounds that are closely related to those described and claimed in our copending application Ser. No. 497,582, filed Aug. 15, 1974, now U.S. Pat. No. 3,940,389, issued Feb. 24, 1976.

BACKGROUND OF THE INVENTION

In one embodiment, the present invention relates to certain novel substituted 4(3H)-oxobenzo-2,1,3-thiadiazine-2,2-dioxide compounds and derivatives. Another embodiment of this invention relates to the utility of these novel substituted 4(3H)-oxobenzo-2,1,3-thiadiazine-2,2-dioxide compounds as herbicides.

The closest prior art includes U.S. Pat. Nos. 3,041,336 and 3,217,001 which disclose certain 4(3H)-oxobenzo-2,1,3-thiadiazine-2,2-dioxides, bearing single halogen, nitro or loweralkylsulfamoyl substituents in the 6- and 7- phenyl ring positions, which have utility as pharmacological agents. Such prior art does not disclose herbicidal utility. The use of 3-(1-methylethyl)-1H-2,1,3-benzothiadiazin-4(3H)-one-2,2-dioxide as a herbicide is also known as well as being described in U.S. Pat. No. 3,708,277.

Other prior art includes German Offenlegungsschrift No. 2,355,113 laid open May 15, 1975, which describes N,N'-disubstituted 2,1,3-benzothiadiazin-4(3H)-one-2,2-dioxide having an alkoxyalkyl group in the 1 position, and showing herbicidal activity.

An object of the present invention is to provide certain new substituted 4(3H)-oxobenzo-2,1,3-thiadiazine-2,2-dioxide compounds which have good herbicidal properties. Another object of the present invention is to provide a method for controlling unwanted plant growth with such substituted 4(3H)-oxobenzo-2,1,3-thiadiazine-2,2-dioxide compounds.

SUMMARY OF THE INVENTION

The present invention is, in one embodiment, directed to novel substituted 4(3H)-oxobenzo-2,1,3-thiadiazine-2,2-dioxide compounds and derivatives corresponding to the formula:

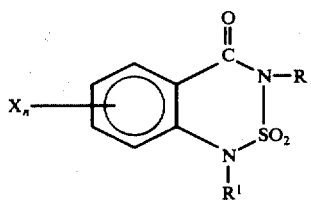

wherein:
each X independently represents halo, YR², Y'CF₂C(Z)₃, CF₃, nitro, or loweralkyl, with the proviso that at least one X is always halo or nitro;
n represents an integer of from 1 to 4, inclusive;
R represents straight or branched alkyl and haloalkyl, each of 1 to 6 carbon atoms; alkenyl, haloalkenyl, alkynyl and haloalkynyl, each of 3 to 6 carbon atoms, cyanoalkyl, alkylthioalkyl or alkoxyalkyl, each of 2 to 6 carbon atoms, cycloalkyl of 3 to 6 carbon atoms, benzyl, phenyl, loweralkylphenyl and halophenyl;

R¹ represents

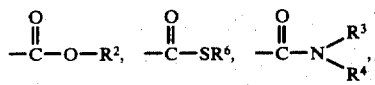

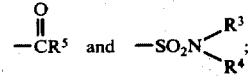

R² represents haloalkyl of 1 to 4 carbon atoms; alkenyl of 3 to 6 carbon atoms; cycloalkyl or 3 to 6 carbon atoms; phenyl, loweralkylphenyl and halophenyl;

R³ represents alkyl or 1 to 4 carbon atoms, and cycloalkyl of 3 to 6 carbon atoms;

R⁴ represents any of R³ and alkoxy containing 1 to 4 carbon atoms, and R³ and R⁴ when taken together constitutes a 4 to 6 carbon heterocyclic radical together with the nitrogen from which each depends; and R⁵ represents alkyl of 1 to 5 carbon atoms, haloalkyl of 1 to 5 carbons, alkenyl, haloalkenyl, alkoxyalkyl or alkylthioalkyl, each of 2 to 6 carbon atoms, cycloalkyl of 3 to 6 carbons, alkoxycarbonylalkyl of 4 to 8 carbon atoms, phenyl, loweralkylphenyl and halophenyl;

R⁶ represents straight or branched alkyl or haloalkyl of 1 to 7 carbon atoms; alkenyl and haloalkenyl of 3 to 6 carbon atoms; cycloalkyl of 3 to 6 carbon atoms; phenyl, loweralkylphenyl and halophenyl;

Y and Y' independently represent a chalcogen group having an atomic number of from 8 to 16, inclusive; and each Z independently represents bromo, chloro, fluoro, or hydrogen.

In an additional embodiment of the invention the present compounds are employed in methods for the control of undesired broadleaf vegetation. Such methods comprise applying a herbicidally effective amount of one or more such compounds to plants, the seeds thereof and/or their habitats. The compositions employed containing the present compounds constitute yet another embodiment of the invention.

For the sake of brevity and convenience, the term "active ingredient(s)" is used hereinafter in this specification to broadly described the present novel substituted 4(3H)-oxobenzo-2,1,3-thiadiazine-2,2-dioxide compounds.

DETAILED DESCRIPTION

As used in the present specification and claims, the term "herbicide" means an active ingredient which, when used in a growth controlling amount, controls or modifies the germination and growth of undesired plants. By a "growth controlling or herbicidally effective amount" is meant an amount of compound which causes a modifying effect upon the germination and growth of plants. Such modifying effects include all deviations from natural development, for example, prevention of germination, reduction in stand, killing, retardation, defoliation, desiccation, regulation, stunting, tillering, and the like. By "plants" it is meant emerging seedlings and established vegetation, including the roots and above-ground portions as well as viable seeds.

The term "loweralkyl" is used herein and in the appended claims to designate a straight or branched chain alkyl or haloalkyl radical containing, where not otherwise expressly defined, from 1 to about 6 carbon atoms, such as, for example, methyl, ethyl, propyl, isopropyl, butyl, isobutyl, tert-butyl, pentyl, hexyl and the like.

The terms "halo" and "halogen", where employed herein, represent iodine, chlorine, fluorine and bromine. The term "cycloalkyl" is employed to mean radicals containing from 3 to about 6 carbon atoms, such as, for example, cyclopropyl, cyclobutyl, cyclopentyl, cyclohexyl, and the like. The term "aryl" is employed to mean phenyl, loweralkylphenyl such as tolyl or xylyl, and halophenyl having up to three of the same or different halogens on the ring. The term "chalcogen" as used herein means those elements of the recognized chalcogen group having an atomic number of from 8 to 16, inclusive, i.e., oxygen and sulfur.

The term "alkenyl" as employed in the present specification and claims designates an alkenyl radical containing from about 3 to about 6 carbon atoms, inclusive, such as, for example, propenyl, 2-methyl propenyl, butenyl, hexenyl and the like which optionally may bear one or more halogen substituents. The term "alkynyl" as used herein and in the appended claims designates an alkynyl radical of from about 3 to about 6 carbon atoms, inclusive, such as, for example, propynyl, 2-methyl propynyl, butynyl, pentynyl, hexynyl and the like which optionally may bear one or more halogen substituents.

The active ingredients of the present invention are normally crystalline solids when substantially pure which are soluble in the usual organic solvents and somewhat insoluble in water. The active ingredients of the instant invention are generally useful as herbicides. With respect to compounds of formula I and the use thereof in herbicidal methods, compounds wherein X is selected from the group consisting of halo and loweralkyl of from one to about 2 carbon atoms are preferred. Additionally, compounds wherein n is 1 to 4, X is selected from the group consisting of loweralkyl and halo, R is loweralkyl and $R^1$ is

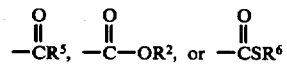

also constitute a preferred class. In each of the foregoing preferred embodiments, at least one X is always halo. With respect to compounds where $n$ is 1, X is a halo or nitro moiety preferably substituted in the 8-ring position, X is preferably a halo moiety, with chloro or fluoro being especially preferred. In all of the foregoing embodiments, compounds wherein R is isopropyl and $R^1$ is

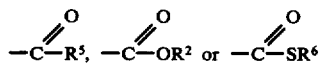

are further preferred.

The active ingredients of the instant invention can be prepared by cyclizing $\beta$-sulphamido carboxylic acid derivatives of the general formula:

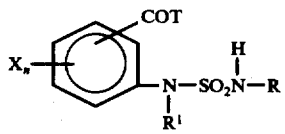

wherein X, $n$, R and $R^1$ are as previously defined and T is a residue which is easily split off such as, for example, a hydroxy, alkoxy or aryloxy or halo group.

In carrying out the preparation of the compounds of the instant invention the selected $\beta$-sulphamido carboxylic acid can be cyclized to the desired corresponding active ingredient of the instant invention with a condensing agent. Representative examples of condensing agents include, for example, phosphorous oxychloride, thionyl chloride or aqueous or alcoholic alkaline solutions such as, for example, sodium methylate and the like. The reaction can be carried out under ambient atmospheric pressures and can be conducted in the presence of inert organic solvents such as, for example, benzene, toluene, xylene, higher ethers, halogenated hydrocarbons and the like. While the reactants can be employed in stoichiometric amounts, an excess amount of the condensing agent may be employed.

The reaction is usually carried out at temperatures of from about 0° to about 150° C., and usually from about 5° to about 110° C. When T is alkoxy the cyclization can be conveniently accomplished in aqueous caustic at 10° to 30° C or in alcoholic alkaline solutions at reflux temperature. The reaction is ordinarily completed in a period of from about 0.25 to about 24 hours. The product can be isolated by methods well understood in the art and appropriately selected according to the compounds having the various $R^1$ substituents specified hereinabove.

The starting materials of formula II can be prepared according to known methods. Procedures for preparing the same as well as literature references to the same are provided in U.S. Pat. No. 3,041,336. Starting materials of Formula II wherein $R^1$ is hydrogen can, following cyclization as previously set forth, be converted to compounds where $R^1$ is other than hydrogen by reacting the same with typical acylating, etc., agents such as, e.g., variously substituted halides of carbonic acid, carboxylic acids, carbamic acids and sulfamic acids, and other types of selected compounds corresponding to the meaning of $R^1$ set forth hereinbefore.

Such reactions can be performed in inert organic solvents such as hydrocarbons, halogenated hydrocarbons, alkanones, the dimethyl ether of ethylene glycol or the like and in the presence of alkali carbonates or bicarbonates. Starting materials of Formula II wherein X represents the $-Y'CF_2C(Z)_3$ moiety are readily prepared by known or analogous procedures disclosed in the literature. For example, starting materials of formula II, wherein X is $-O(S)CF_2CHCl_2$, are readily prepared by sparging 1,1-dichloro-2,2-difluoroethylene into a mixture of sodium methyl hydroxy(thiol)anthranilate in acetone at a temperature of from about 0° to about 10° C. for a period of about 1 to about 2 hours. Following the completion of the reaction, the solvent is removed by evaporation under reduced pressure and the desired starting material recovered.

Those compounds wherein each Z is chloro or bromo are readily prepared by further photochemically halogenating the thus recovered starting material with an appropriate halogenating agent, such as, for example $Cl_2$, ClBr and the like in known procedures using a solvent such as carbon tetrachloride or a heterogenous mixture employing water. Those starting materials wherein Z is fluoro are prepared by reacting the starting materials wherein Z is chloro or bromo with a molten antimony fluoro-chloro compound at temperatures of from about 80° to about 120° C. for periods of ½ to 2 hours.

Other substituents in the 5, 6, 7 and 8 ring positions of the starting materials of Formula II may, depending upon the resistance of such substituent to the preceding reactions, be introduced after cyclization of the same to the corresponding 4(3H)-oxobenzo-2,1,3-thiadiazine-2,2-dioxide compound.

The following examples illustrate the present invention and the manner by which it can be practiced but, as such, should not be construed as limitations upon the overall scope of the same.

EXAMPLE 1

1H-2,1,3-Benzothiadiazin-4(3H)-one: 1-acetyl-8-chloro-3-(1-methylethyl)-2,2-dioxide To 70 ml of methylene chloride was added 7.0 g (0.255 mole) of 8-chloro-3-(1-methylethyl)-1H-2,1,3-benzothiadiazin-4(3H)-one-2,2-dioxide and 7 ml of triethylamine. A solution consisting of 2.0 ml (0.028 mole) of acetyl chloride in 30 ml $CH_2Cl_2$ was added dropwise over a 0.5 hr period, the reaction temperature being maintained between 25°–30° C. After 30 minutes an additional 2.0 ml of acetyl chloride in 30 ml $CH_2Cl_2$ was added and the resultant mixture allowed to stir overnight.

The mixture was extracted with two 100 ml-portions of $H_2O$ and two 100 ml-portions of 5% aqueous potassium carbonate. The organic layer was dried with $MgSO_4$, filtered and the solvent removed in vacuo affording 7.9 g of crude product as a solid. Recrystallization was accomplished by dissolving the solid in 70 ml of ether, filtering, and adding 50 ml of $CH_3OH$. The ether was removed with stirring under a nitrogen atmosphere and the resultant mixture filtered to afford analytically pure 1-acetyl-8-chloro-3-(1-methylethyl)-1H-2,1,3-benzothiadiazin-4(3H)-one-2,2-dioxide having a melting point of 87° C (with decomposition).

EXAMPLE 2

1H-2,1,3-Benzothiadiazin-4(3H)-one: 8-chloro-3-(1-methylethyl)-1-(1-oxobutyl)-,2,2-dioxide In a 500 ml, 3-necked flask equipped with a magnetic stirrer, a condenser with a drying tube and a thermometer were placed 10.0 g of 1H-2,1,3-Benzothiadiazin-4(3H)-one: 8-chloro-3-(1-methylethyl)-, 2,2-dioxide (.036 mole), 150 ml of acetonitrile and 4.26 g of potassium tertiary butoxide (0.038 mole). The reaction was heated to reflux temperature. The heat was removed, and the reaction was allowed to return to room temperature (about 1 hour). To the reaction was added dropwise a solution of 3.84 g of butyryl chloride (0.036 mole) in 100 ml of acetonitrile during a one hour period. The reaction was stirred over the week-end at room temperature. The mixture was filtered, and the acetonitrile was removed from the filtrate in vacuo. The residual crude oil was taken up in 250 ml of methylene chloride and washed with 5% $NaHCO_3$ (two 200 ml-portions) and with 200 ml of $H_2O$. The methylene chloride extract was dried over $Na_2SO_4$, and the methylene chloride was removed in vacuo affording 10.29 g of light brown oil. The crude oil was taken up in 25 ml of methanol, stirred for 1 hour at room temperature, cooled and filtered affording 7.11 g of white solid, m.p. 74.5°–76.5° C.

EXAMPLE 3

1H-2,1,3-Benzothiodiazine-1-carbothioic acid: 8-Chloro-3,4-dihydro-3-(1-methylethyl)-4-oxo-; S-Methyl Ester; 2,2-dioxide To 100 ml of acetonitrile was added 10 g (0.036 mole) of 8-chloro-3-(1-methylethyl)-1H-2,1,3-benzothiadiazin-4(3H)-one-2,2-dioxide and 4.43 g of potassium t-butoxide. The mixture was heated to reflux, cooled to 50° C and 3.5 ml (0.04 mole) of methyl chlorothioformate in 50 ml of acetonitrile was added dropwise over a 0.5 hr. period. The mixture was heated at 50° C overnight. It was cooled, filtered, and the solvent removed from the filtrate in vacuo. The crude product was recrystallized from methanol to afford analytically pure product, m.p. 117.5°–119.5° C.

EXAMPLES 4 and 5

The following derivatives were prepared in a similar manner: 1H-2,1,3-Benzothiadiazine-1-carbothioic acid: 8-chloro-3,4-dihydro-3-(1-methylethyl)-4-oxo-; S-Propyl Ester; 2,2-Dioxide. m.p. = 69.5°–70.5° C. 1H-2,1,3-Benzothiadiazine-1-carbothioic acid: 8-chloro-3,4-dihydro-3-(1-methylethyl)-4-oxo-; S-Ethyl Ester; 2,2-Dioxide. m.p. = 76.5°–77° C.

Other active ingredients of Formula I are similarly prepared by employing procedures analogous to those set forth in Examples 1 and 2 avove and the foregoing teachings of the specification by cyclizing a selected $\beta$-sulphamido carboxylic acid with a condensing agent and are set forth in Table I below:

TABLE I

| Cmpd. No. | X | Ring Position | R | $R^1$ |
|---|---|---|---|---|
| 6 | Cl | 8 | s-$C_4H_9$ | $-C(=O)-N(CH_3)_2$ |
| 7 | Cl | 8 | $-C_2H_5$ | $-C(=O)-N(C_2H_5)_2$ |
| 8 | F | 8 | i-Pr* | $-C(=O)-CH_3$ |
| 9 | F | 8 | i-Pr | $-C(=O)-C_3H_7$ |
| 10 | Cl | 8 | i-Pr | $-C(=O)-C_5H_{11}$ |
| 11 | Cl | 8 | i-Pr | $-SO_2N(CH_3)_2$ |
| 12 | Cl | 8 | i-Pr | $-C(=O)-S-C_6H_5$ |
| 13 | Cl | 8 | i-Pr | $-C(=O)-C_6H_5$ |
| 14 | Cl | 8 | i-Pr | $-C(=O)-(2\text{-thienyl})$ |
| 16 | Cl | 8 | i-Pr | $-C(=O)-OCH_2-CH=CH_2$ |
| 17 | Cl | 8 | i-Pr | $-C(=O)-O-(2\text{-thienyl})$ |
| 18 | F | 8 | i-Pr | $-C(=O)-O-C_6H_5$ |
| 19 | Cl | 8 | i-Pr | $-C(=O)-O-C_6H_4-CH_3$ |
| 20 | Cl | 8 | i-Pr | $-C(=O)-N(\text{morpholino})$ |

TABLE I-continued

| Cmpd. No. | X | Ring Position | R | R¹ |
|---|---|---|---|---|
| 21 | Cl | 8 | i-Pr | -C(=O)-N-CH₂ / CH₂ CH₂ \ CH₂ (morpholine-like ring with N-CH₂CH₂-CH₂-CH₂) |
| 22 | NO₂ | 8 | i-Pr | -C(=O)-N(CH₃)₂ |
| 23 | di-Cl | 7,8 | i-Pr | -C(=O)-CH₃ |
| 24 | Br | 8 | i-Pr | -C(=O)-CH₃ |
| 25 | CF₃, Cl | 6,8 | i-Pr | -C(=O)-CH₃ |
| 26 | CH₃, Cl | 7,8 | i-Pr | -C(=O)-CH₃ |
| 27 | CH₃, Cl | 6,8 | i-Pr | -C(=O)-CH₃ |
| 28 | —OCH₃, Cl | 6,8 | i-Pr | -C(=O)-CH₃ |
| 29 | —OCF₂CH₂Cl, Cl | 6,8 | i-Pr | -C(=O)-CH₃ |
| 30 | —SCH₃, Cl | 6,8 | i-Pr | -C(=O)-N(CH₃)₂ |
| 31 | Cl | 7 | i-Pr | -C(=O)-SCH₃ |
| 32 | F | 8 | i-Pr | -C(=O)-SC₂H₅ |
| 33 | F | 8 | i-Pr | -C(=O)-SC₃H₇ |

*i-Pr = isopropyl

The compounds disclosed in the present invention have been found to be suitable for use both in the general post-emergent and pre-emergent control of weeds or other unwanted vegetation. For all such uses, unmodified active ingredients of the present invention can be employed. However, the present invention embraces the use of active ingredients with a material known in the art as an adjuvant in solid or liquid form. Thus, for example, an active ingredient can be dispersed on a finely divided solid and employed therein as a dust. Also, the active ingredients or a solid composition comprising the active ingredients can be dispersed in water, typically with the aid of a wetting agent, and the resulting aqueous suspension employed as a spray. In other procedures, the active ingredient can be employed as a constituent of organic liquid compositions, oil-in-water and water-in-oil emulsions, or water dispersions, with or without the addition of wetting, dispersing, or emulsifying agents.

Suitable adjuvants of the foregoing type are well known to those skilled in the art. The methods of applying the solid or liquid herbicidal formulations similarly are well known to the skilled artisan.

As organic solvents there can be employed hydrocarbons, e.g. benzene, toluene, xylene, kerosene, diesel fuel, fuel oil, and petroleum naphtha, ketones such as acetone, methyl ethyl ketone and cyclohexanone, chlorinated hydrocarbons such as carbon tetrachloride, chloroform, trichloroethylene, and perchloroethylene, esters such as ethyl acetate, amyl acetate and butyl acetate, ethers, e.g., ethylene glycol monomethyl ether and diethylene glycol monomethyl ether, alcohols, e.g., methanol, ethanol, isopropanol, amyl alcohol, ethylene glycol, propylene glycol, butyl Carbitol acetate and glycerine. Mixtures of water and organic solvents, either as solutions or emulsions, can be employed.

The active ingredients can also be applied as aerosols, e.g., by dispersing them in air by means of a compressed gas such as dichlorodifluoromethane or trichlorofluoromethane and other Freons and Genetrons, for example.

The active ingredients of the present invention can also be applied with adjuvants or carriers such as talc, pyrophyllite, synthetic fine silica, attapulgus clay, kieselguhr, chalk, diatomaceous earth, lime, calcium carbonate, bentonite, fuller's earth, cottonseed hulls, wheat flour, soybean flour, pumice, tripoli, wood flour, walnut shell flour, redwood flour and lignin.

As stated, it is frequently desirable to incorporate a surface active agent in the compositions of the present invention. Such surface active or wetting agents are advantageously employed in both the solid and liquid compositions. The surface active agent can be anionic, cationic or nonionic in character.

Typical classes of surface active agents include alkyl sulfonate salts, alkylaryl sulfonate salts, alkylaryl polyether alcohols, fatty acid esters of polyhydric alcohols and the alkylene oxide addition products of such esters, and addition products of long chain mercaptans and alkylene oxides. Typical examples of such surface active agents include the sodium alkylbenzene sulfonates having 10 to 18 carbon atoms in the alkyl group, alkylphenol ethylene oxide condensation products, e.g., p-isooctylphenol condensed with 10 ethylene oxide units, soaps, e.g., sodium stearate and potassium oleate, sodium salt of propylnaphthalene sulfonic acid, di(2-ethylhexyl)-ester of sodium sulfosuccinic acid, sodium lauryl sulfate, sodium decane sulfonate, sodium salt of the sulfonated monoglyceride of coconut fatty acids, sorbitan sesquioleate, lauryl trimethyl ammonium chloride, octadecyl trimethyl ammonium chloride, polyethylene glycol lauryl ether, polyethylene glycol esters of fatty acids and rosin acids, e.g., Ethofat 7 and 13, sodium N-methyl-N-oleyl taurate, Turkey Red Oil, sodium dibutyl naphthalene sulfonate, sodium lignin sulfonate, polyethylene glycol stearate, sodium dodecylbenzene sulfonate, tertiary dodecyl polyethylene glycol thioether (nonionic 218), long chain ethylene oxide-propylene oxide condensation products, e.g., Pluronic 61 (molecular weight 1,000), polyethylene glycol ester of tall oil acids, sodium octyl phenoxyethoxyethyl sulfate, tris(polyoxyethylene)sorbitan monostearate (Tween 60), and sodium dihexyl sulfosuccinate.

The concentration of the active ingredients in liquid compositions generally is from about 1 to about 95 percent by weight or more. Concentrations of from about 5 to about 50 weight percent are often employed. In dusts or dry formulations, the concentration of the active ingredient can be from about 0.01 to about 95 weight percent or more; concentrations of from about 1 to about 50 weight percent are often conveniently employed. In compositions to be employed as concentrates, the active ingredient can be present in a concentration of from about 5 to about 98 weight percent. The active ingredient compositions can also contain other compatible additaments, for example fertilizers, phytotoxicants, plant growth regulants, pesticides and the like.

The active ingredients are most usefully brought into commerce in the form of (1) a wettable powder in which one or more of the active ingredients in finely divided form are blended with one of the wetting agents or surfactants above listed with or without combination also with a finely divided absorptive clay or other absorptive inert adjuvant or carriers as listed above; (2) a flowable concentrate which corresponds largely to a "pre-wet" wettable powder composition having as high as 50 percent solids content and containing water and/or other appropriate liquid as well understood in the formulation art and (3) an emulsifiable concentrate in which one or more of the active ingredients are dissolved in an organic solvent, such as one of those listed, in admixture with a wetting, dispersing or emulsifying agent such as those described above, whereby the concentrate will readily become an emulsion on dilution with water.

In general treating operations for the modification and control of vegetative growth plants and seeds and/or their habitats are contacted with sufficient amounts of a composition containing one or more active ingredients to provide a dosage rate of from about 0.5 to about 20 or more pounds of active ingredient per acre but more preferably about 0.5 to 4 pounds per acre. It is to be understood, however, that all of the active ingredients claimed and compositions containing the same may not be equally effective at similar concentrations against the same plant species. Thus, higher or lower rates than those stated may be necessary in certain instances.

So as to illustrate clearly the phytotoxic properties of the various active ingredients of the present invention, group of controlled greenhouse experiments is described below.

Various species of plants were planted in beds of good agricultural soil in a greenhouse. After the plants had emerged and grown to a height of about 2-6 inches, a portion of the plants were sprayed with an aqueous mixture, made by mixing a selected active ingredient and emulsifier or dispersant with water, employing sufficient amounts of the treating composition to provide application rates of about 8.0 pounds per acre. Other portions of the plants were left untreated to serve as controls.

After a period of 2 weeks the effect of the test ingredient on the plants was evaluated by a comparison with the control group of plants. As a result of such operations, it was found that a 8-chloro-1-acetyl-3-(1-methylethyl)-1H-2,1,3-benzothiadiazin-4(3H)-one-2,2-dioxide test ingredient gave substantially complete control of annual morning glory, nutsedge, cotton, pigweed and velvet leaf as did the 1H-2,1,3-benzothiadiazin-1-carbothioic acid: 8-chloro-3,4-dihydro-3-(1-methylethyl)-4-oxo-; S-methyl ester; 2,2-dioxide test ingredient.

We claim:
1. A compound of the formula:

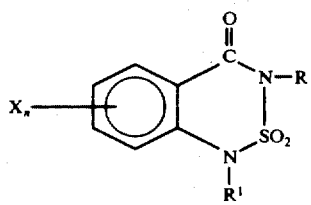

wherein:
each X independently represents halo, $YR^2$, $Y'CF_2C(Z)_3$, $CF_3$, nitro, or loweralkyl, with the proviso that at least one X is always halo or nitro;
$n$ represents an integer of from 1 to 4, inclusive;
R represents straight or branched alkyl and haloalkyl, each of 1 to 6 carbon atoms; alkenyl, haloalkenyl, alkynyl and haloalkynyl, each of 3 to 6 carbon atoms, cyanoalkyl, alkylthioalkyl or alkoxyalkyl, each of 2 to 6 carbon atoms, cycloalkyl of 3 to 6 carbon atoms, benzyl, phenyl, loweralkylphenyl and halophenyl;
$R^1$ represents

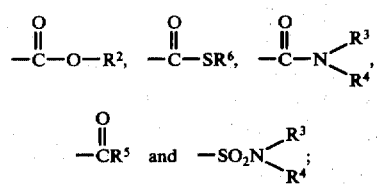

$R^2$ represents haloalkyl of 1 to 4 carbon atoms; alkenyl of 3 to 6 carbon atoms; cycloalkyl or 3 to 6 carbon atoms; phenyl, loweralkylphenyl and halophenyl;
$R^3$ represents alkyl of 1 to 4 carbon atoms, and cycloalkyl of 3 to 6 carbon atoms;
$R^4$ represents any of $R_3$ and alkoxy containing 1 to 4 carbon atoms, and $R^3$ and $R^4$ when taken together constitutes a 4 to 6 carbon heterocyclic radical together with the nitrogen from which each depends; and
$R^5$ represents alkyl of 1 to 5 carbon atoms, haloalkyl of 1 to 5 carbons, alkenyl, haloalkenyl, alkoxyalkyl or alkylthioalkyl, each of 2 to 6 carbon atoms, cycloalkyl of 3 to 6 carbons, alkoxycarbonylalkyl of 4 to 8 carbon atoms, phenyl, loweralkylphenyl and halophenyl;
$R^6$ represents straight or branched alkyl or haloalkyl of 1 to 7 carbon atoms; alkenyl and haloalkenyl of 3 to 6 carbon atoms; cycloalkyl of 3 to 6 carbon atoms; phenyl, loweralkylphenyl and halophenyl;
Y and Y' independently represent a chalcogen group having an atomic number of from 8 to 16, inclusive; and
each Z independently represents bromo, chloro, fluoro, or hydrogen.

2. The compound of claim 1 wherein X is selected from the group consisting of halo and lower alkyl of from 1 to 2 carbon atoms.

3. The compound of claim 1 wherein $n$ is 1 to 4, each X is selected from the group consisting of loweralkyl and halo, respectively, R is loweralkyl and $R^1$ is one of

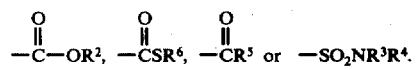

4. The compound of claim 3 wherein X is halo and $n$ is 1 or 2.

5. The compound of claim 4 wherein R is isopropyl.

6. The compound of claim 1 which is 3,4-dihydro-8-chloro-3-(1-methylethyl)-4-oxo-1H-2,1,3-benzothiadiazine-1-carbothioic acid, s-propyl ester, 2,2-dioxide.

7. The compound of claim 1 which is 3,4-dihydro-8-chloro-3-(1-methylethyl)-4-oxo-1H-2,1,3-benzothiadiazine-1-carbothioic acid, s-methyl ester, 2,2-dioxide.

8. The compound of claim 1 which is 3,4-dihydro-8-chloro-3-(1-methylethyl)-4-oxo-1H-2,1,3-benzothiadiazine-1-carbothioic acid, s-ethyl ester, 2,2-dioxide.

9. The compound of claim 1 which is 1-acetyl-8-chloro-3-(1-methylethyl)-1H-2,1,3-benzothiadiazin-4(3H)-one-2,2-dioxide.

10. The compound of claim 1 which is 1-oxobutyl-8-chloro-3-(1-methylethyl)-1H-2,1,3-benzothiadiazin-4(3H)-one-2,2-dioxide.

11. A method for controlling undesired plants which comprises applying to said plants and/or their habitats a herbicidally effective amount of a compound corresponding to the formula:

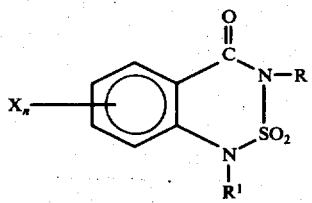 (I)

wherein:
each X independently represents halo, $YR^2$, $Y'CF_2C(Z)_3$, $CF_3$, nitro, or loweralkyl with the proviso that at least one X is always halo or nitro;
n represents an integer of from 1 to 4, inclusive;
R represents straight or branched alkyl and haloalkyl, each of 1 to 6 carbon atoms; alkenyl, haloalkenyl, alkynyl and haloalkynyl, each of 3 to 6 carbon atoms, cyanoalkyl, alkylthioalkyl or alkoxyalkyl, each of 2 to 6 carbon atoms, cycloalkyl of 3 to 6 carbon atoms, benzyl, phenyl, loweralkylphenyl and halophenyl;
$R^1$ represents

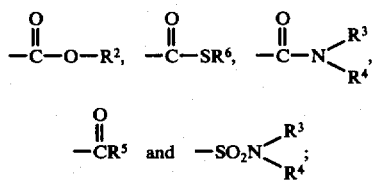

$R^2$ represents haloalkyl of 1 to 4 carbon atoms; alkenyl of 3 to 6 carbon atoms; cycloalkyl or 3 to 6 carbon atoms; phenyl, loweralkylphenyl and halophenyl;
$R^3$ represents alkyl or 1 to 4 carbon atoms, and cycloalkyl of 3 to 6 carbon atoms;
$R^4$ represents any of $R^3$ and alkoxy containing 1 to 4 carbon atoms, and $R^3$ and $R^4$ when taken together constitutes a 4 to 6 carbon heterocyclic radical together with the nitrogen from which each depends; and
$R^5$ represents alkyl of 1 to 5 carbon atoms, haloalkyl of 1 to 5 carbons, alkenyl, haloalkenyl, alkoxyalkyl or alkylthioalkyl, each of 2 to 6 carbon atoms, cycloalkyl of 3 to 6 carbons, alkoxycarbonylalkyl of 4 to 8 carbon atoms, phenyl, loweralkylphenyl and halophenyl;
$R^6$ represents straight or branched alkyl or haloalkyl of 1 to 7 carbon atoms; alkenyl and haloalkenyl of 3 to 6 carbon atoms; cycloalkyl of 3 to 6 carbon atoms; phenyl, loweralkylphenyl and halophenyl;
Y and Y' independently represent a chalcogen group having an atomic number of from 8 to 16, inclusive; and each Z independently represents bromo, chloro, fluoro, or hydrogen.

12. The method of claim 11 wherein X is selected from the group consisting of halo, and loweralkyl of from one to two carbon atoms.

13. The method of claim 11 wherein the compound is applied to the foilage of an existing plant structure.

14. The method of claim 11 wherein R is loweralkyl of from 1 to 6 carbon atoms.

15. The method of claim 11 wherein n is 1 to 4, each X is selected from the group consisting of loweralkyl and halo, respectively, R is loweralkyl and $R^1$ is one of

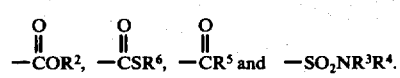

16. The method of claim 15 wherein X is halo and n is 1 or 2.

17. The method of claim 16 wherein R is isopropyl.

18. The method of claim 11 wherein the compound is 3,4-dihydro-8-chloro-3-(1-methylethyl)-4-oxo-1H-2,1,3-benzothiadiazine-1-carbothioic acid, s-propyl ester, 2,2-dioxide.

19. The method of claim 11 wherein the compound is 3,4-dihydro-8-chloro-3-(1-methylethyl)-4-oxo-1H-2,1,3-benzothiadiazine-1-carbothioic acid, s-methyl ester, 2,2-dioxide.

20. The method of claim 11 wherein the compound is 3,4-dihydro-8-chloro-3-(1-methylethyl)-4-oxo-1H-2,1,3-benzothiadiazine-1-carbothioic acid, s-ethyl ester, 2,2-dioxide.

21. The method of claim 11 wherein the compound is 1-acetyl-8-chloro-1H-2,1,3-benzothiadiazine-4(3H)-one-2,2-dioxide.

22. The method of claim 11 wherein the compound is 1-oxobutyl-8-chloro-1H-chloro-1H-2,1,3-benzothiadiazine-4(3H)-one-2,2-dioxide.

23. A herbicidal composition comprising a herbidical amount of a compound corresponding to the formula:

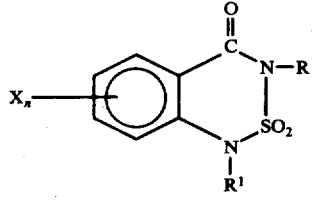 (I)

wherein:
each X independently represents halo, $YR^2$, $Y'CF_2C(Z)_3$, $CF_3$, nitro, or loweralkyl, with the proviso that at least one X is always halo or nitro;
n represents an integer of from 1 to 4, inclusive;
R represents straight or branched alkyl and haloalkyl, each of 1 to 6 carbon atoms; alkenyl, haloalkenyl, alkynyl and haloalkynyl, each of 3 to 6 carbon atoms, cyanoalkyl, alkylthioalkyl or alkoxyalkyl, each of 2 to 6 carbon atoms, cycloalkyl of 3 to 6 carbon atoms, benzyl, phenyl, loweralkylphenyl and halophenyl;
$R^1$ represents

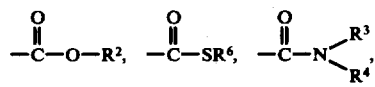

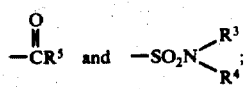 and $-SO_2N\begin{smallmatrix}R^3\\R^4\end{smallmatrix}$;

R² represents haloalkyl of 1 to 4 carbon atoms; alkenyl of 3 to 6 carbon atoms; cycloalkyl or 3 to 6 carbon atoms; phenyl, loweralkylphenyl and halophenyl;

R³ represents alkyl or 1 to 4 carbon atoms; and cycloalkyl of 3 to 6 carbon atoms;

R⁴ represents any of R³ and alkoxy containing 1 to 4 carbon atoms, and R³ and R⁴ when taken together constitutes a 4 to 6 carbon heterocyclic radical together with the nitrogen from which each depends; and R⁵ represents alkyl of 1 to 5 carbon atoms, haloalkyl of 1 to 5 carbons, alkenyl, haloalkenyl, alkoxyalkyl or alkylthioalkyl, each of 2 to 6 carbon atoms, cycloalkyl of 3 to 6 carbon, alkoxycarbonylalkyl of 4 to 8 carbon atoms, phenyl, loweralkylphenyl and halophenyl;

R⁶ represents straight of branched alkyl or haloalkyl of 1 to 7 carbon atoms; alkenyl and haloalkenyl of 3 to 6 carbon atoms; cycloalkyl of 3 to 6 carbon atoms; phenyl, loweralkylphenyl and halophenyl;

Y and Y' independently represent a chalcogen group having an atomic number of from 8 to 16, inclusive; and each Z independently represents bromo, chloro, fluoro, or hydrogen.

24. The composition as in claim 23 wherein X is selected from the group consisting of halo and loweralkyl of from 1 to 2 carbon atoms.

25. The composition as in claim 23 wherein n is 1 to 4, each X is selected from the group consisting of loweralkyl and halo, respectively, R is loweralkyl and R¹ is one of

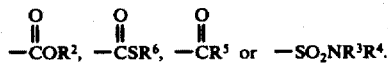

26. The composition as in claim 25 wherein X is halo and n is 1 or 2.

27. The composition as in claim 26 wherein R is isopropyl.

28. The composition as in claim 23 wherein the compound is 3,4-dihydro-8-chloro-3-(1-methylethyl)-4-oxo-1H-2,1,3-benzothiadiazine-1-carbothioic acid, s-propyl 29. The composition as in claim 23 wherein the compound is 3,4-dihydro-8-chloro-3-(1-methylethyl)-4-oxo-1H-2,1,3-benzothiadiazine-1-carbothioic acid, s-methyl ester, 2,2-dioxide.

30. The composition as in claim 23 wherein the compound is 3,4-dihydro-8-chloro-3-(1-methylethyl)-4-oxo-1H-2,1,3-benzothiadiazine-1-carbothioic acid, s-ethyl ester, 2,2-dioxide.

31. The composition as in claim 23 wherein the compound is 1-acetyl-8-chloro-3-(1-methylethyl)-1H-2,1,3-benzothiadiazin-4(3H)-one-2,2-dioxide.

32. The composition as in claim 23 wherein the compound is 1-oxobutyl-8-chloro-3-(1-methylethyl)-1H-2,1,3-benzothiadiazin-4(3H)-one-2,2-dioxide.

33. The method for the selective control of undesired plants in the presence of soybean plants which comprises contacting said plants with a herbicidally effective amount of a compound corresponding to the formula:

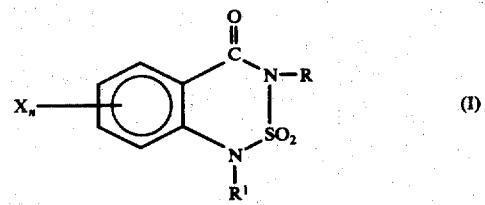 (I)

wherein:
each X independently represents halo, YR², Y'CF₂C(Z)₃, CF₃, nitro, or loweralkyl, with the proviso that at least one X is always halo or nitro;
n represents an integer of from 1 to 4, inclusive;
R represents straight or branched alkyl and haloalkyl, each of 1 to 6 carbon atoms; alkenyl, haloalkenyl, alkynyl and haloalkynyl, each of 3 to 6 carbon atoms, cyanoalkyl, alkylthioalkyl or alkoxyalkyl, each of 2 to 6 carbon atoms, cycloalkyl of 3 to 6 carbon atoms, benzyl, phenyl, loweralkylphenyl and halophenyl;
R¹ represents

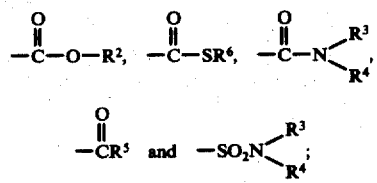

R² represents haloalkyl of 1 to 4 carbon atoms; alkenyl of 3 to 6 carbon atoms; cycloalkyl or 3 to 6 carbon atoms; phenyl, loweralkylphenyl and halophenyl;

R³ represents alkyl or 1 to 4 carbon atoms, and cycloalkyl of 3 to 6 carbon atoms;

R⁴ represents any of R³ and alkoxy containing 1 to 4 carbon atoms, and R³ and R⁴ when taken together constitutes a 4 to 6 carbon heterocyclic radical together with the nitrogen from which each depends; and R₅ represents alkyl of 1 to 5 carbon atoms, haloalkyl of 1 to 5 carbons, alkenyl, haloalkenyl, alkoxyalkyl or alkylthioalkyl, each of 2 to 6 carbon atoms, cycloalkyl of 3 to 6 carbons, alkoxycarbonylalkyl of 4 to 8 carbon atoms, phenyl, loweralkylphenyl and halophenyl;

R⁶ represents straight or branched alkyl or haloalkyl of 1 to 7 carbon atoms; alkenyl and haloalkenyl of 3 to 6 carbon atoms; cycloalkyl of 3 to 6 carbon atoms; phenyl, loweralkylphenyl and halophenyl;

Y and Y' independently represent a chalcogen group having an atomic number of from 8 to 16, inclusive; and each Z independently represents bromo, chloro, fluoro, or hydrogen.

* * * * *